United States Patent
Toribio et al.

(10) Patent No.: US 10,493,022 B2
(45) Date of Patent: Dec. 3, 2019

(54) ALCOHOLIC EXTRACT OF THE AERIAL PARTS OF ANTHYLLIS VULNERARIA, METHOD FOR OBTAINING SAME, AND COSMETIC OR PHARMACEUTICAL COMPOSITION CONTAINING SAME

(71) Applicant: CHANEL PARFUMS BEAUTE, Neuilly sur Seine (FR)

(72) Inventors: Alix Toribio, Saint Ouen (FR); Lionel Weinberg, Le Perreux-sur-Marne (FR); Annie Lerisson, Montmagny (FR); Maeva Gillet, Paris (FR); Emmanuelle Bouissou-Cadio, Clichy sous Bois (FR); François Lejeune, Andeville (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 0 days.

(21) Appl. No.: 16/230,419

(22) Filed: Dec. 21, 2018

(65) Prior Publication Data
US 2019/0201319 A1    Jul. 4, 2019

(30) Foreign Application Priority Data
Dec. 21, 2017 (EP) .................... 17306870

(51) Int. Cl.
*A61K 36/00* (2006.01)
*A61K 8/9789* (2017.01)
*A61Q 19/02* (2006.01)

(52) U.S. Cl.
CPC ............ *A61K 8/9789* (2017.08); *A61Q 19/02* (2013.01); *A61K 2236/333* (2013.01)

(58) Field of Classification Search
None
See application file for complete search history.

(56) References Cited

FOREIGN PATENT DOCUMENTS

| FR | 2 699 073 | 6/1994 |
| FR | 2 831 444 | 5/2003 |
| FR | 2 834 211 | 7/2003 |
| FR | 2 837 702 | 10/2003 |

OTHER PUBLICATIONS

Sterk et al, Some Observations on the Antho Cyanins in the Flowers Oanthyllis-Vulneraria Leguminosae Fabaceae. Acta Botanica Neerlandica, (1977) vol. 26, No. 4, pp. 349-352 (Year: 1977).*
European Search Report, EP 17 30 6870, dated Apr. 25, 2018.
Hirano A: "Skin external preparation for use as cosmetics, comprises extracts of e.g. Aeschynomene indica, Alysicarpus vaginalis, Anthyllis vuleneraria, Butea monosperma, Judas tree and Campylotropis trigonoclada", WPI / Thomson, Sep. 28, 2001 (Sep. 28, 2001), XP002415823, * abrege *.
"Gesture of Beauty Kit", GNPD, Mintel, janvier 2015 (Jan. 2015), XP002765376, * abrege *.
"Natural Plus Sun Stick SPF", GNPD. Mintel, Jun. 2017 (Jun. 2017), XP002777039, * abrege *.
"After sun lotion", GNPD; Mintel, Sep. 2008 (Sep. 2008). XP002692716, [extrait le Jan. 9, 2008] * abrege *.

* cited by examiner

*Primary Examiner* — Qiuwen Mi
(74) *Attorney, Agent, or Firm* — Young & Thompson

(57) ABSTRACT

Disclosed is an alcoholic extract of aerial parts of *Anthyllis vulneraria*, method for obtaining same, a cosmetic or dermatological composition containing same, as well as the cosmetic and dermatological uses thereof, in particular in depigmenting the skin.

13 Claims, 2 Drawing Sheets

ALCOHOLIC EXTRACT OF THE AERIAL PARTS OF ANTHYLLIS VULNERARIA, METHOD FOR OBTAINING SAME, AND COSMETIC OR PHARMACEUTICAL COMPOSITION CONTAINING SAME

BACKGROUND OF THE INVENTION

Field of the Invention

The invention relates to an extract of aerial parts of *Anthyllis vulneraria*, method for obtaining same, a cosmetic or pharmaceutical composition containing same, as well as various cosmetic uses.

Description of the Related Art

The colour of human skin is a function of various factors and in particular of the seasons of the year, the race and the gender. It is mainly determined by the nature and the concentration of melanin produced by the melanocytes. Melanocytes are the specialised dendritic cells that, by the intermediary of particular organelles, the melanosomes, which synthesise melanin. Furthermore, at different periods during their life, certain people see on the skin and more especially on the hands, darker and/or more coloured spots, providing the skin with heterogeneity. These spots are also due to a substantial concentration of melanin in the keratinocytes located on the surface of the skin.

The use of inoffensive topical depigmenting substances that are effective is very particularly sought for the treating of regional hyperpigmentations due to melanocyte hyperactivity such as idiopathic melasmas, that occur during pregnancy ("pregnancy mask" or chloasma) or an estrogen plus progestin contraception, localised hyperpigmentations due to benign melanocyte hyperactivity and proliferation, such as brown age spots referred to as actinic lentigos, accidental hyperpigmentations, possibly due to photosensitisation or to post-lesional cicatrisation, as well as certain leukodermas, such as vitiligo. For the latter (cicatrisations that can result in a scar giving the skin a whiter aspect), failing able to repigment the damaged skin, depigmentation of the areas of normal residual skin is completed in order to give the overall skin a homogeneous white complexion.

A substance is recognised as being depigmenting or anti-depigmenting if it acts directly on the vitality of the epidermal melanocytes where melanogenesis takes place, and/or if it interferes with one of the steps in the biosynthesis of melanin either by inhibiting one of the enzymes involved in melanogenesis, or by inserting itself as a structural analogue of one of the chemical compounds of the synthesis chain of melanin, a chain that can then be blocked and thus ensure depigmentation.

A link has recently been established between pigmentation and the Sestrines gene family (SESN)—in particular SESN1 and SESN2. Indeed, as established by the applicant in application EP2015/072080, their levels of gene expression in melanocytes exposed to UV radiation were modulated. Moreover, many scientific publications demonstrate that SESNs also intervene in limiting the damage induced by the oxydative stress.

The cosmetic substances that are most often used for depigmenting are more particularly ascorbic acid and the derivatives thereof, including ascorbyle glucoside, as well as certain plant extracts (in particular liquorice).

There however remains the need for a novel whitening agent of human skin that is effective and that is of natural origin, and well tolerated.

SUMMARY OF THE INVENTION

In this respect, the Applicant has now found that an alcoholic extract of aerial parts of *Anthyllis vulneraria*, obtained by a particular method, has, through its action of decreasing the synthesis of melanin of melanocytes, interesting activities with regards to the pigmentation and unification of the complexion of the skin. Indeed, as demonstrated in examples, the alcoholic extract of aerial parts of *Anthyllis vulneraria* according to the invention have interesting cosmetic properties: it allows for a whitening action of the skin, in particular by induction of the expression of SESN2 in melanocytes and keratinocytes. Its action on inducing the expression of SESN2 can also allow for the prevention and/or the attenuation of alterations of the skin due to ageing.

The invention therefore relates to, according to a first aspect, an alcoholic extract of aerial parts of *Anthyllis vulneraria*, able to be obtained by a method comprising the following steps:
 a) extracting the aerial parts of *Anthyllis vulneraria*, with at least one alcoholic solvent;
 b) decanting of the mixture obtained in a) for at least 10 h;
 c) filtering of the decanted mixture obtained in b); and
 d) removing the solvent from the filtrate obtained, then final diluting in another alcoholic solvent.

Such an extract is thus called, in this application, extract according to the invention.

The invention also relates to a method for extracting aerial parts of *Anthyllis vulneraria*, comprising the following steps:
 a) extracting the aerial parts of *Anthyllis vulneraria*, with at least one alcoholic solvent;
 b) decanting of the mixture obtained in a) for at least 10 h;
 c) filtering of the decanted mixture obtained in b); and
 d) removing the solvent from the filtrate obtained, then final diluting in another alcoholic solvent.

The invention also relates to a cosmetic or dermatological composition comprising, in a cosmetically or pharmaceutically acceptable vehicle, an alcoholic extract of aerial parts of *Anthyllis vulneraria* according to the invention. The term cosmetically or pharmaceutically acceptable vehicle means a medium that is compatible with the skin, mucosa and appendages. Preferably, the cosmetic or dermatological composition according to the invention is suitable for topical application.

The method for obtaining the extract according to the invention thus comprises the following steps:
 a) extracting the aerial parts of *Anthyllis vulneraria*, with at least one alcoholic solvent;
 b) decanting of the mixture obtained in a) for at least 10 h;
 c) filtering of the decanted mixture obtained in b); and
 d) removing the solvent from the filtrate obtained, then final diluting in another alcoholic solvent.

The raw material implemented is constituted of the aerial parts of *Anthyllis vulneraria*.

*Anthyllis vulneraria* (*Anthyllis vulneraria*) also called Vulneraria, Tea of the Alps, Sand clover, is an annual or perennial ephemeral herbaceous plant, of the family Fabaceae. It is a low plant 20 to 60 cm high extending as ground cover. It has dense rosettes of dark green leaves, covered with silky hairs. Its inflorescences are yellow-orange, grouped into heads, wholly calyx, appearing from May to August, until September at higher elevations. It is a heliophilous species that grows in sunny places, often at the seacoast and in dry prairies, mountain lawns and woodland areas. It has a large altitudinal range, up to 3200 m, a high tolerance for cold and drought.

With fast growth, and a deeply anchored root system, it ensures rapid stabilisation of the topsoil. It is a pioneer plant, it can use substrates poor in organic material and colonise damaged lands. Like all Fabaceae, its ability to fix nitrogen from the air can rapidly enrich the soil, thus favouring the growth of the other plants.

There are many subspecies such as

*Anthyllis vulneraria* L. subsp. *alpestris* (Kit.) Asch. & Gr.
*Anthyllis vulneraria* L. subsp. *bocsii*
*Anthyllis vulneraria* L. subsp. *maritima*
*Anthyllis vulneraria* L. subsp. *rubrifolia*
*Anthyllis vulneraria* L. subsp. *vulneraria*

The aerial parts of *Anthyllis vulneraria* used according to the invention are typically chosen from the flowers, the leaves, the stems and mixtures thereof. Preferably, the aerial parts used are a mixture of flowers, leaves and stems of *Anthyllis vulneraria*. Preferably, these aerial parts are dried beforehand, then ground or reduced into pieces in the usual way, in order to, preferably, have the form of a powder with a size less than 2 cm.

In the step a), the aerial parts are subjected to an extraction by one or several alcoholic solvents, for example chosen from:

$C_1$-$C_4$ monohydric alcohols, such as for example methanol, ethanol or isopropanol; and diols, such as for example propylene glycol, 1,3-propanediol or dipropylene glycol.

Preferably, the alcoholic solvent is a monohydric alcohol comprising from 2 to 4 carbon atoms, more preferably ethanol.

The extraction is generally carried out by immersing or by gently stirring the aerial parts in one or several of the solvents mentioned hereinabove at temperatures ranging, for example, from ambient temperature to 80° C., for a duration of about 30 minutes to 8 h. Preferably, the extracting of the step a) is carried out for a duration between 2 and 6 hours, at a temperature between 40° C. and 60° C.

In particular, the weight ratio of *Anthyllis vulneraria*/alcoholic solvent is between 1/1 and 1/20, and preferably is 1/10.

According to a particular embodiment, the step a) of extracting is carried out twice.

The mixture obtained in the step a) is then decanted for at least 10 h: this is the step b). Preferably, the incubating of the step b) is carried out for a duration between 12 h and 30 h, at a temperature between 2° C. and 30° C. More preferably, the decanting is carried out for one night, preferably for 12 h to 15 h, at a temperature between 4 and 20° C.

The mixture obtained in the step a) can be screened before the step b) of decanting in order to remove the plant residues. Advantageously, the screening is carried out over a screen with a mesh size between 50 µm and 100 µm.

The decanted mixture obtained at the end of the step b) is then filtered in order to remove the insoluble substances: this is the step c). Preferably, the filtering of the extract obtained in b) is carried out over a 4 µm membrane. A liquid, preferably transparent, filtrate is obtained.

Finally, the solvent present in the liquid filtrate is removed, then the rest of the filtrate is diluted in another alcoholic solvent: this is the step d). The alcoholic solvent used in the step d) is called "other alcoholic solvent", because it is different from the alcoholic solvent used in the step a). Taking account of this limitation, the alcoholic solvent is typically chosen from the same group as the one of the step a), i.e. from $C_1$-$C_4$ monohydric alcohols and diols.

Preferably, the removal of the solvent of the step d) is done via evaporation. Preferably, the final dilution is carried out in a diol, preferably 1,3-propanediol. In particular, the final dilution can be carried out as a mixture of water and 1,3-propanediol. For example, a mixture of solvents constituted of 80% of 1,3-propanediol, 10% of water is added to 10% of powder (weight/weight). In order to facilitate the solubilisation of the filtrate, ethanol can be added and removed by evaporation.

Preferably, between the steps c) and d), a step of discolouring of the filtrate obtained in c) is added. The discolouration can be done through adsorption of pigments such as the chlorophylls and xanthophylls present in the filtrate over activated charcoal. This step of discolouring can be followed by one or several steps of filtrating of the discoloured filtrate obtained, in particular of filtering over a filtration media until a filtration threshold of 1 µm.

According to a particular embodiment, the method according to the invention furthermore implements a step e) of filtering, in particular until a filtration threshold of 4 µm.

Preferably, the alcoholic extract of aerial parts of *Anthyllis vulneraria* according to the invention is able to be obtained by a method comprising the following steps:

a) a first extracting of a mixture of flowers, leaves and stems of *Anthyllis vulneraria*, dried and ground beforehand, with ethanol, at a temperature between 50° C. and 70° C. for 2 h to 5 h the screening between 50 µm and 100 µm;

a') a second extraction of the product obtained in the step a) with ethanol, at a temperature between 50° C. and 70° C. for 2 h to 5 h, then screening at 100 µm, b) decanting of the mixture of filtrates obtained in a) and a') for at least 12 h at a temperature between 2° C. and 30° C.;

c) filtering of the decanted mixture obtained in b), in order to obtain a filtrate;

discolouration of the filtrate obtained in c) by adsorption on activated charcoal; then filtering of the discoloured filtrate to a threshold of filtration of 1 µm; and d) removing of the ethanol from the filtrate obtained by evaporation, then final diluting in 1,3-propanediol, preferably in a water/1,3-propanediol mixture, e) filtering to a filtration threshold of 4 µm.

Advantageously, the extract implemented according to the invention is of a clear colour.

Also, said extract has a form that is sufficiently concentrated to be able to be used without causing the formulation problems that are usually encountered with the concentrations required to obtain an activity in the cosmetic or dermatological compositions in the form of an emulsion, and without having a dark colour, contrary to the plant extracts obtained by the usual methods, when they are in concentrated form.

Therefore, the extract according to the invention can be used directly for the preparing of a cosmetic or dermatological composition.

According to a later aspect, the invention relates to the cosmetic use of an alcoholic extract of aerial parts of *Anthyllis vulneraria* according to the invention, as a depigmentation agent, and/or whitening agent and/or lightening agent, to unify the skin complexion, and/or for correcting pigmentary imperfections.

Indeed, advantageously, it was found that the alcoholic extract of aerial parts of *Anthyllis vulneraria* according to the invention has several activities of interest with regards to physiological mechanisms that make it possible to decrease the synthesis of melanin.

The invention therefore relates to, more particularly, the cosmetic use of an alcoholic extract of aerial parts of *Anthyllis vulneraria* according to the invention as an melanin synthesis inhibitor agent.

It was also found that, advantageously, the alcoholic extract of aerial parts of *Anthyllis vulneraria* according to the invention has an advantageous activity with regards to the expression of SESN2 in melanocytes and/or keratinocytes.

The invention also relates to the use of an alcoholic extract of aerial parts of *Anthyllis vulneraria* according to the invention as an activator agent of the expression of SESN2 in melanocytes and/or keratinocytes.

The invention also relates to, more particularly, the cosmetic use of an alcoholic extract of aerial parts of *Anthyllis vulneraria* according to the invention for the depigmentation and/or the whitening of the skin, in particular via its inhibiting action of the synthesis of melanin.

The invention further relates to the cosmetic use of an alcoholic extract of aerial parts of *Anthyllis vulneraria* according to the invention as an antioxidant and/or agent that improves the cutaneous microcirculation, and/or for the prevention and/or the attenuation of alterations of the skin due to ageing.

The invention also relates to, according to a later aspect, a cosmetic or dermatological composition comprising, in a cosmetically or pharmaceutically acceptable vehicle, an alcoholic extract of aerial parts of *Anthyllis vulneraria* according to the invention. Preferably, said extract is present in the cosmetic or dermatological composition at a rate of 0.001 to 10% by total weight of the composition, in particular at a rate of 0.01 to 10%, more preferably 0.1 to 10% by total weight of the composition. Said cosmetic or dermatological composition can in particular, be suitable for topical application.

Advantageously, said cosmetic or dermatological composition can have the form of a powder, an emulsion, a microemulsion, a nanoemulsion, a suspension, a solution of a lotion, of a creme, of an aqueous or hydroalcoholic gel, a foam, a serum, a solution or a dispersion for aerosol, or a dispersion of lipidic vesicles.

In the case of an emulsion, this can be a water in oil or oil in water emulsion.

The cosmetic or dermatological composition according to the invention can also include a solvent chosen according to the various ingredients and the form of administration.

By way of examples, mention can be made of water (more preferably demineralised water), an alcohol such as ethanol, or an ether of diethylene glycol such as ethoxydiglycol or monomethyl ethers of diethylene glycol.

Said cosmetic composition can also include at least one usual additive in the field, such as for example at least one compound chosen from an emollient or humectant agent, a gelling and/or thickening agent, a surfactant, an oil, an active agent, a colorant, a preservative, an antioxidant agent, an active agent, an organic or inorganic powder, a sunscreen and a perfume.

In particular, said composition can contain:

One or several emollient or humectant agents, that can be chosen for example from glycerine, glycols, hydrosoluble silicones such as the one sold under the name KF6011 (Shin Etsu) and hydrosoluble Jojoba, such as the one sold under the name Resplanta jojoba (Res pharma).

Said emollient or humectant agent can be present in the composition at a content of about from 0 to 30%, more preferably 2 to 10% by weight, in relation to the total weight of the composition.

One or several gelling and/or thickening agents of the aqueous phase, chosen for example from cellulose derivatives, gums of plant origin (guar, carob, alginates, carrageenans, pectin), of microbial origin (xanthan), clays (laponite), the materials identified by the INCI names "ammonium acryloyldimethyltaurate/vp copolymer" and "ammonium acryloyldimethyl-taurate/beheneth-25 methacrylate copolymer" (such as for example those sold under the names Aristoflex AVC and HMB by Clariant).

Said gelling and/or thickening agent can be present in the composition at a content of about from 0 to 10% by weight, in relation to the total weight of the composition.

One or several surfactants, more preferably non-ionic, present in a content of about from 0 to 8%, more preferably 0.5 to 3% by weight, in relation to the total weight of the composition.

One or several liquid fatty substances at ambient temperature, commonly called volatile or non-volatile, hydrocarbon or silicone, linear, cyclical or branched oils, for example, isododecane, cyclopentadimethylsiloxane, dimethicones, isononyl isononanoate or pentaerythrityl tetraisostearate, more preferably at a rate of 0 to about 10%, more preferably 0.5 to 5% by weight, in relation to the total weight of the composition.

One or several active agents, of natural or synthetic origin, having a biological activity, for example chosen from vitamins, trace elements, allantoin, plant proteins, plant extracts, hydrating agents, anti-ageing agents, antioxidants, agents favouring radiance and mixtures of the latter. In particular, the active agent is chosen from a water of the *vanilla planifolia* fruit, niacinamide, hyaluronic acid and the derivatives thereof, a yeast extract and mixtures of the latter.

One or several hydrosoluble colorants such as, for example, ponceau disodium salt, alizarin green disodium salt, quinoline yellow, amaranth trisodium salt, tartrazine disodium salt, rhodamine monosodium salt, fuchsin disodium salt or xanthophyll, more preferably at a rate of 0 to about 2% by weight, in relation to the total weight of the composition.

Other additives usually used in cosmetics can also be present in the composition according to the invention, in particular preservatives, antioxidant agents or perfumes that are well known in the technical field.

Those skilled in the art can choose, from all of these possible additives, the nature as well as the quantity of those that will be added to the composition, in such a way that the latter retains all of its properties.

DESCRIPTION OF THE PREFERRED EMBODIMENTS

Figure 1:
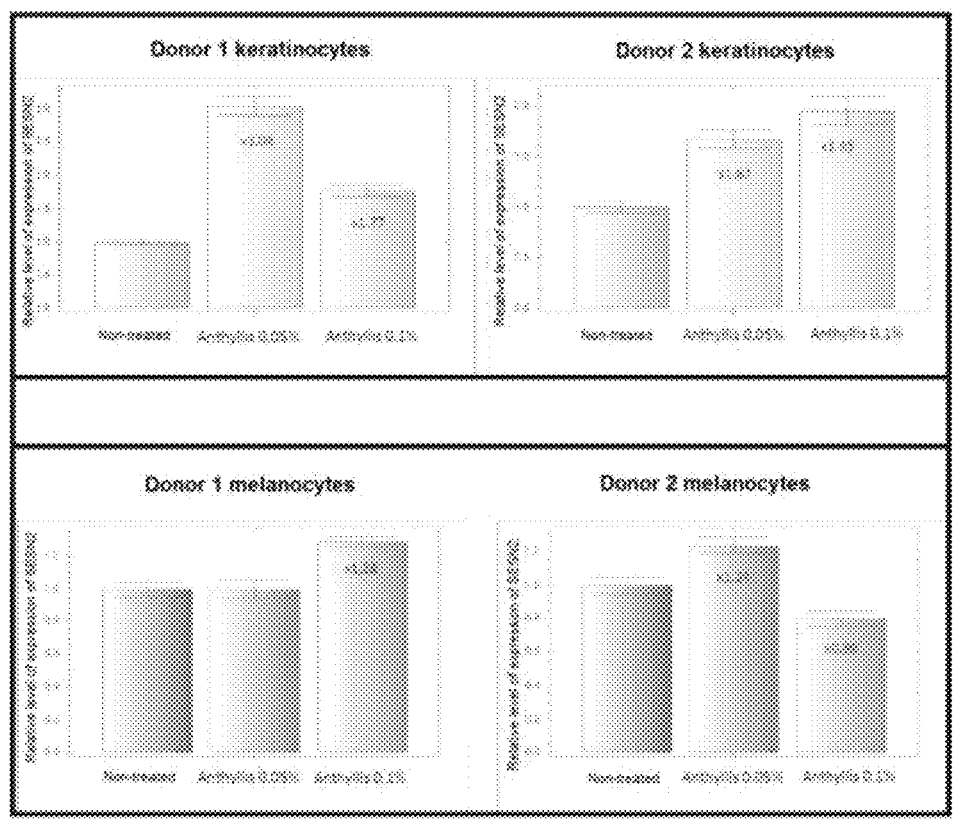
FIG. 1 illustrates the evaluation of the effect of the alcoholic extract of *Anthyllis vulneraria* on the gene expression of SESN2.

The invention is shown in a non-limiting way by the examples hereinbelow.

Example 1: Preparation of an Alcoholic Extract of Aerial Parts of *Anthyllis vulneraria* According to the Invention An alcoholic extract of aerial parts of *Anthyllis vulneraria* according to the invention is prepared by a method comprising the following steps:
  a) a first extracting of a mixture of flowers, leaves and stems of *Anthyllis vulneraria*, dried and ground beforehand, with ethanol, at a temperature of 60° C. for at least 2 h and screening from 50 μm to 100 in order to obtain the filtrate 1;
  a') a second extracting of the product obtained in the step a) on the grains retained during the screening of the step a), with ethanol, at a temperature of 60° C. for at least 2 h, then the mixture is screened between 50 μm and 100 μm in order to remove the plant residues in order to obtain the filtrate 2
  b) decanting of the mixture of filtrates 1 and 2 obtained in a) and a') for one night (at least 12 h) at a temperature between 2° C. and 25° C.;
  c) filtering of the decanted mixture obtained in b) to the threshold of 1 μm, in order to obtain a filtrate;
    discolouration of the filtrate obtained in c) by adsorption on activated charcoal; then
    filtering of the discoloured filtrate until the threshold of 1 μm; and
  d) removing of the ethanol from the filtrate obtained by evaporation, then final dilution in a water/1,3-propanediol mixture 12%/88%,
  e) filtering to a filtration threshold of 4 μm.

Example 2: Test of the Cytotoxicity of the Alcoholic Extract of *Anthyllis vulneraria* in Normal Human Keratinocytes Protocol:

Normal human epidermal keratinocytes (PromoCell) coming from juvenile donors were cultivated in 96-well plates until a confluence close to 75%. The cellules were then incubated with various concentrations of the alcoholic extract of *Anthyllis vulneraria*, each concentration in triplicate, for 48 h. The cytotoxicity was evaluated using the Cell Titer96 Aqueous One Solution Cell Proliferation Assay (Promega), based on the capacity of the viable cells to reduce the colourless/yellow tetrazolium salts to an intensely brown coloured formazan derivative. The cells were incubated with the tetrazolium at 37° C. for 30 minutes and the absorbance of the formazan formed was read at 490 nm.

Results:

The cytotoxicity of the alcoholic extract of *Anthyllis vulneraria* was evaluated at various concentrations between 0.1 and 0.0125% (table 1 hereinbelow).

TABLE 1

| Cells | Sample | | % Control |
|---|---|---|---|
| Keratinocytes | Non-treated control | | 100 ± 23 |
| | *Anthyllis* | 0.1% | 90 ± 18 |
| | | 0.05% | 128 ± 19 |
| | | 0.025% | 129 ± 34 |
| | | 0.0125% | 113 ± 22 |

The alcoholic extract of *Anthyllis vulneraria* is not toxic for keratinocytes at all concentrations tested.

These concentrations will therefore be used in the following experiments on the two cell types (keratinocytes and melanocytes).

Example 3: Evaluation of the Effect of the Alcoholic Extract of *Anthyllis vulneraria* on the Gene Expression of SESN2

Protocol:

The keratinocytes and melanocytes were cultivated in a 6-well plate until a confluence close to 75% before being treated for 24 h at the following concentrations of the alcoholic extract of *Anthyllis vulneraria:*
  0.1%
  0.05%

The total RNA was extracted using the RNeasy kit (Qiagen, cat#74182) in accordance with the manufacturer's protocol, quantified via spectrophotometry (Thermo Fisher Scientific, Multiskan GO) and retrotranscribed into cDNA using iScript Reverse Transcription Supermix kit (Biorad, cat#1708840).

The cDNA was then used in real-time quantitative PCR (qRT-PCR, Biorad, CFX96) for the analysis of the gene expression of SESN2 by using the suitable Taqman probes (Thermo Fisher Scientific) and probes corresponding to housekeeping genes for standardisation.

The results are expresses as "fold change" of expression of SESN2 of the condition treated in relation to the control condition.

Results:

In the 2 cell types, we observe an induction of the expression of SESN2 (donor and dependent dose, as shown in FIG. 1), of approximately ×3.04 max in keratinocytes and ×1.28 max in melanocytes.

It is therefore possible to conclude that the alcoholic extract of *Anthyllis vulneraria* is an effective ingredient for regulating the stress response, remodelling the extracellular matrix, photoageing, pigmentation and therefore in the homeostasis of the skin.

Example 4: Determination of the Effect of the Alcoholic Extract of *Anthyllis vulneraria* on the Synthesis of Melanin in Human Melanocytes in Culture Protocol:

Melanocytes were cultivated in 6-well plates until a confluence of 50% max.

The cells were incubated with various concentrations of the alcoholic extract of *Anthyllis vulneraria* (non-toxic concentrations ranging from 0.1 to 0.0125% tested in example 1), in duplicate, for 5 days with a renewal treatment of the active every 2 days. The cells were then lysed and the melanin solubilised in NaOH 1 M at 60° C. for 1 h.

For the extracting of the intracellular melanin, the cells were lysed in NaOH 1 M, centrifuged at 12,000 rpm for 5 minutes, and the absorbance of the clear supernatants was measured at 490 nm. The content in melanin was standardised in relation to total proteins per well at 595 nm (Biorad Protein Assay, Biorad).

Kojic acid, of which the action is widely documented in the inhibition of the synthesis of melanin, was used as a positive control.

Figure 2:
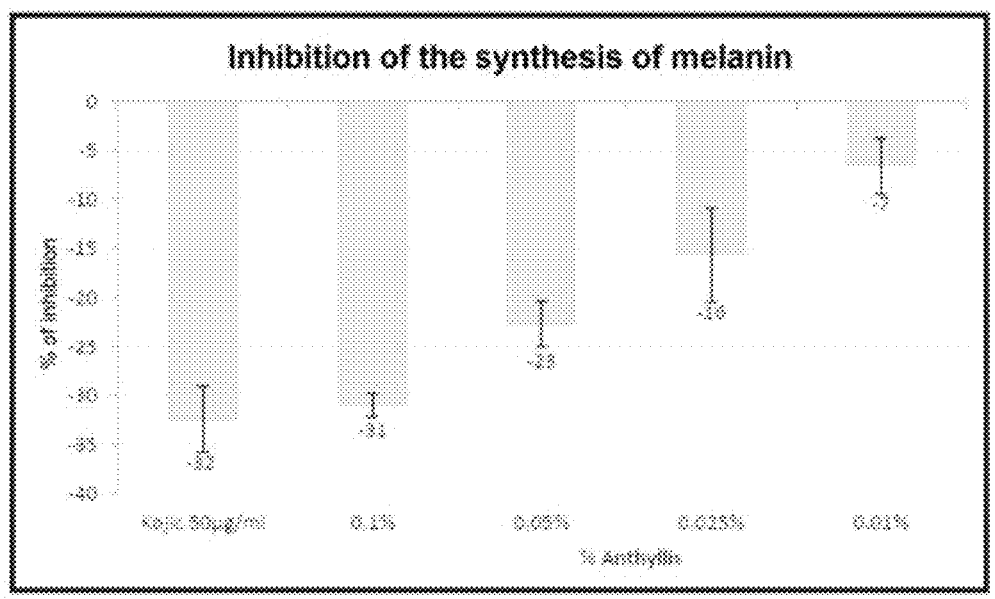
FIG. 2 illustrates the effect of the alcoholic extract of *Anthyllis vulneraria* on the synthesis of melanin in human melanocytes in culture.

Results:

The results, shown in FIG. 2, are represented as a % of the non-treated control which is set to 100%.

The melanin is the chromophore of human skin synthesised by the melanocytes of the epidermis and are responsible mainly for the colour of the skin. The possible effect of the alcoholic extract of *Anthyllis vulneraria* on the pigmentation of the skin was evaluated by chemical quantification of melanin in the treated and non-treated cells.

The alcoholic extract of *Anthyllis vulneraria* at the concentration of 0.1% inhibits by 31±1.2% the content in melanin of the melanocytes in relation to the non-treated cells.

It results from this test that the alcoholic extract of *Anthyllis vulneraria* modulate the content in melanin of the cultivated melanocytes and can therefore decrease the level of pigmentation of the skin (therefore act as a depigmentation agent).

Figure 3:
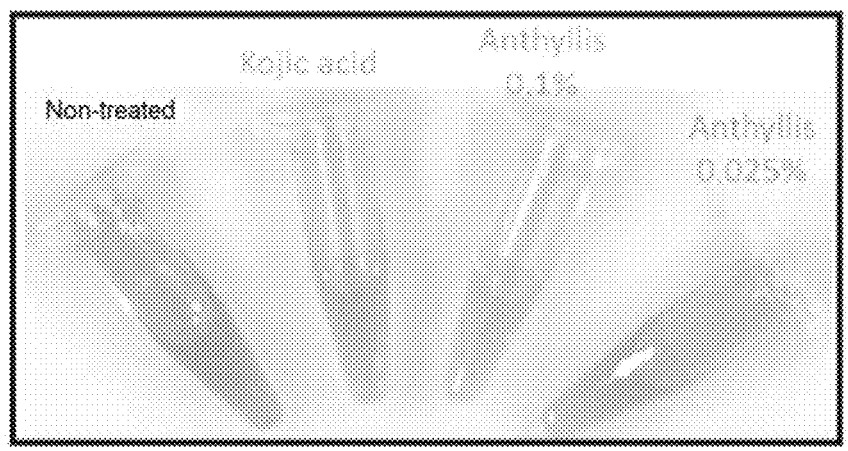
FIG. 3 illustrates the appearance of lysates of the cells treated with *Anthyllis* compared to control cells.

Visually, the appearance of lysates of the cells treated with *Anthyllis* is clearly lighter than the control cells (as shown in FIG. 3).

Example 5: Cosmetic Compositions

5A—Gel Creme Oil/Water Emulsion

| INCI name | (% W/W) |
|---|---|
| Jojoba esters | 1-10 |
| Hydrogenated coconut oil | 1-10 |
| Moringa oil/hydrogenated moringa oil esters (FLORALIPIDS MORINGA BUTTER) | 1-10 |
| *Butyrospermum parkii* butter (LIPEX SHEASOFT) | 1-10 |
| *Camellia kissi* seed oil | 1-10 |
| *Butyrospernum parkii* butter extract (LIPEX SHEA TRIS) | 1-10 |
| Pentaerythrityl stearate/caprate/caprylate/adipate (SUPERMOL S-SO) | 0.5-5 |
| Cetyl ethylhexanoate | 1-5 |
| Octyl palmitate | 1-5 |
| Diisostearyl dimer dilinoleate (SCHERCEMOL DISD) | 1-10 |
| Octyldodecyl myristate | 1-5 |
| Hydrogenated lecithin | 0.1-5 |
| Cetearyl alcohol & cetearyl glucoside | 0.1-7 |
| Glyceryl stearate & PEG-100 stearate | 0.1-5 |
| CARBOMER | 0.01-5 |
| BIOSACCHARIDE GUM-1 | 1-10 |
| Methyl methacrylate crosspolymer (MAKIBEADS 150) | 0.1-10 |
| Sodium hyaluronate | 0.01-3 |
| Glycerin | 1-30 |
| Polyquaternium-51 | 1-10 |
| Adenosine | 0.1-0.5 |
| Niacinamide | 0.1-5 |
| *Tremella fuciformis* polysaccharide | 0.1-5 |
| Palmitoyl Tripeptide-1 & Palmitoyl Tetrapeptide-7 | 1-5 |
| *Secale Cereale* (Rye) Seed Extract | 1-5 |
| Alcoholic extract of *Anthyllis vulneraria* | 0.01-10 |
| Ascorbyl glucoside | 0.001-5 |
| Glycols (Caprylyl Glycol and/or Pentylene Glycol and/or Butylene Glycol and/or propanediol) | 0.1-10 |
| Water | Qs 100 |

5b—Creme Oil/Water Emulsion

| INCI name | (% w/w) |
|---|---|
| Behenyl alcohol | 1-5 |
| Cetyl alcohol | 0.1-5 |
| Phenyl trimethicone | 1-5 |
| Dimethicone & Dimethicone/Vinyl Dimethicone Crosspolymer | 1-30 |
| Ectoin | 0.1-5 |
| PPG-2 myristyl ether propionate | 1-10 |
| Nanofine Titanium Dioxide | 1-20 |
| Zinc Dioxide | 1-20 |
| Diethylamino Hydroxybenzoyl Hexyl Benzoate (Uvinul A+) | 1-5 |
| Bis-Ethylhexyloxyphenol Methoxyphenyl Triazine (Tinosorb S) | 1-5 |
| (Tinosorb M) | 1-5 |
| Ethyl hexyl Methoxycinnamate | 1-7.5 |
| Polysilicone -11 | 1-5 |
| Silica | 1-5 |
| Polymethylsilsesquioxane | 1-5 |
| C20-22 alkyl phosphate & C20-22 alcohols | 0.5-5 |
| Glyceryl stearate & PEG-100 stearate | 0.5-5 |
| sodium acrylate/sodium acryloyldimethyltaurate copolymer | 0.1-5 |
| Hydrogenated starch hydrolysate & maltooligosyl glucoside | 0.1-10 |
| Xanthan Gum | 0.01-2 |
| Agar | 0.1-5 |
| Adenosine | 0.1-0.5 |
| Niacinamide | 0.1-5 |
| *Tremella fuciformis* polysaccharide | 0.1-5 |
| Palmitoyl Tripeptide-1 & Palmitoyl Tetrapeptide-7 | 1-5 |
| *Secale Cereale* (Rye) Seed Extract | 1-5 |
| Alcoholic extract of *Anthyllis vulneraria* | 0.01-10 |
| Ascorbyl glucoside | 0.001-5 |
| Water | Qs 100 |

These compositions can be applied every day, morning and/or evening, on the skin.

The invention claimed is:

1. Method for extracting aerial parts of *Anthyllis vulneraria*, comprising the following steps:
    a) extracting the aerial parts of *Anthyllis vulneraria*, with at least one alcoholic solvent;
    b) decanting of the mixture obtained in a) for at least 10 h;
    c) filtering of the decanted mixture obtained in b); and
    d) removing the solvent from the filtrate obtained, then final diluting in another alcoholic solvent.

2. The method according to claim 1, wherein the alcoholic solvent of the step a) is a monohydric alcohol comprising from 1 to 4 carbon atoms.

3. The method according to claim 2, wherein the alcoholic solvent of the step a) is ethanol.

4. The method according to claim 1, wherein the extracting of the step a) is carried out for a duration between 2 and 6 hours, at a temperature between 40° C. and 60° C.

5. The method according to claim 1, wherein the aerial parts are chosen from the flowers, the leaves, the stems and mixtures thereof.

6. The method according to claim 1, wherein the step a) is carried out twice.

7. The method according to claim 1, wherein the decanting of the step b) is carried out for a duration between 12 h and 30 h, at a temperature between 2° C. and 30° C.

8. The method according to claim 1, wherein the mixture obtained at the step a) is screened before the step b) of decanting.

9. The method according to claim 8, wherein the mixture obtained at the step a) is screened over a screen with a mesh size between 50 μm and 100 μm.

10. The method according to claim 1, wherein, between the steps c) and d), is added a step of discolouration of the filtrate obtained in c), followed by a step or several steps of filtration of the discoloured filtrate obtained.

11. The method according to claim 10, wherein the step of discolouration is performed by adsorption on active charcoal.

12. The method according to claim 1, wherein the removing of the step d) is done via evaporation, then the final dilution is carried out in 1,3-propanediol.

13. The method according to claim 1, wherein the method implements a step e) of filtration.

* * * * *